(12) United States Patent
Furukawa et al.

(10) Patent No.: US 8,313,902 B2
(45) Date of Patent: Nov. 20, 2012

(54) MAGNETIC FINE PARTICLES HAVING LOWER CRITICAL SOLUTION TEMPERATURE

(75) Inventors: Hirotaka Furukawa, Yokohama (JP);
Noriyuki Ohnishi, Yokohama (JP);
Kazunori Kataoka, Tokyo (JP);
Katsuhiko Ueno, Tsukuba (JP)

(73) Assignee: JNC Corporation, Tokyo (JP)

( * ) Notice: Subject to any disclaimer, the term of this patent is extended or adjusted under 35 U.S.C. 154(b) by 1159 days.

(21) Appl. No.: 12/219,266

(22) Filed: Jul. 18, 2008

(65) Prior Publication Data
US 2008/0293118 A1 Nov. 27, 2008

Related U.S. Application Data

(62) Division of application No. 11/030,149, filed on Jan. 7, 2005, now abandoned, which is a division of application No. 10/362,174, filed as application No. PCT/JP01/07119 on Aug. 20, 2001, now Pat. No. 7,695,905.

(30) Foreign Application Priority Data

Aug. 21, 2000 (JP) ............................ P.2000-249774

(51) Int. Cl.
*C12Q 1/68* (2006.01)
(52) U.S. Cl. ........................................... 435/6.1
(58) Field of Classification Search ............ 435/6.1
See application file for complete search history.

(56) References Cited

U.S. PATENT DOCUMENTS

| | | | |
|---|---|---|---|
| 5,136,095 A | 8/1992 | Tarnowski et al. | |
| 5,445,971 A | 8/1995 | Rohr | |
| 5,795,719 A | 8/1998 | Richard et al. | |
| 6,521,341 B1 | 2/2003 | Elaissari et al. | |
| 7,052,917 B1 | 5/2006 | Ohnishi et al. | |

FOREIGN PATENT DOCUMENTS

| | | |
|---|---|---|
| EP | 0302715 | 2/1989 |
| JP | 3020271 | 1/2000 |
| WO | 87/02063 | 4/1987 |
| WO | 90/06045 | 6/1990 |
| WO | 98/12717 | 3/1998 |

OTHER PUBLICATIONS

International Search Report issued Dec. 4, 2001 in International Application No. PCT/JP01/07119.
Supplementary European Search Report issued Jun. 15, 2004 in European Application No. 01 95 6971.
International Preliminary Examination Report in International Application No. PCT/JP01/07119, Sep. 10, 2002.
Bjørn-Ivar Haukanes et al., "Application of Magnetic Beads in Bioassays", Bio/Technology, Nature Publishing Co., New York, vol. 11, No. 1, pp. 60-63, 1993, XP 000609039, ISSN: 0733-222X.
Akihiko Kondo et al., "Preparation of Thermo-Sensitive Magnetic Hydrogel Microspheres and Application to Enzyme Immobilization", Journal of Fermentation and Bioengineering, vol. 84, No. 4, pp. 337 to 341, Oct. 25, 1997.
Akihiko Kondo, et al., "Development and application of thermo-sensitive magnetic immunomicrospheres for antibody purification", Applied Microbiology and Biotechnology, vol. 41, No. 1, pp. 99 to 105, Mar. 1994.
Hirotaka Furukawa et al., "Jogen Rinkai Youeki Ondo wo Yuusuru Shinki Jisei Biryuushi", Kobunchi Gakkai Yokoushuu, vol. 49, No. 10, pp. 3079 to 3080, Sep. 8, 2000.

*Primary Examiner* — Jezia Riley
(74) *Attorney, Agent, or Firm* — Wenderoth, Lind & Ponack, L.L.P.

(57) ABSTRACT

The present invention relates to magnetic fine particles having a lower critical solution temperature to which at least one substance selected from biotin and avidin is immobilized, and a method of converting a substance, a method of separating or concentrating a microorganism, a method of modifying a denatured protein, a method of detecting a nucleic acid, a separating agent, and a method of separating a biological substance using the same.

7 Claims, No Drawings

MAGNETIC FINE PARTICLES HAVING LOWER CRITICAL SOLUTION TEMPERATURE

This application is a Divisional Application of Ser. No. 11/030,149, filed Jan. 7, 2005, now abandoned, which is a Divisional Application of Ser. No. 10/362,174, filed Feb. 21, 2003, now U.S. Pat. No. 7,695,905, which is 371 application of PCT/JP01/07119, filed Aug. 20, 2001.

TECHNICAL FIELD

The present invention relates to magnetic fine particles having a lower critical solution temperature, and a method of converting a substance, a method of separating or concentrating a microorganism, a method of modifying a denatured protein, a method of detecting a nucleic acid, a separating agent, and a method of separating a biological substance, each using the magnetic fine particles.

BACKGROUND ART

As described in Clin. Microbiol. Rev., 1994, pp. 43-54, there are many attempts to separate a variety of biological molecules and microorganisms by immobilizing antibodies or pairing bases to magnetic fine particles. As the magnetic fine particles for use in these methods, those having a particle size of 1 μm or more are usually used in consideration of the time for recovering them with a magnet. However, since the surface area decreases as the particle size increases, the efficiency is a big problem in the case that a small molecule such as a protein or nucleic acid is tried to separate.

As a method for solving the problem of particle size, Applied. Microbiol. Biotechnol., 1994, Vol. 41, pp. 99-105 and Journal of fermentation and Bioengineering, 1997, Vol. 84, pp. 337-341 have reported that magnetic fine particles having a lower critical solution temperature (hereinafter referred to as "LCST") and a particle size of about 100 to 200 nm are obtained by polymerizing polyisopropylacrylamide having an LCST in the presence of magnetic fine particles and that the magnetic fine particles is possible to recover easily through their aggregation caused by raising the solution temperature to the LCST or higher even though the particle size of the magnetic fine particles is smaller than that of conventional particles.

In the reports, methacrylic acid is copolymerized at the polymerization of polyisopropylacrylamide, bovine serum albumin is then immobilized to the carboxylic acid using a carbodiimide after completion of the polymerization, and purification of bovine serum albumin in serum is attempted.

However, this method requires immobilization of an enzyme, an antibody, or the like to the polymer on the magnetic particles depending on individual intended uses and also requires removal of unreacted substances, so that it is necessary to carry out operations for purification and hence the method is not versatile. Moreover, in the method, since a nucleic acid should be directly bound to a protein or the like, the immobilization of a nucleic acid is very difficult.

As described above, in the conventional technology, the usefulness of the magnetic fine particles having an LCST is recognized in the field of separating agents and the like, but there is a problem of poor versatility.

DISCLOSURE OF THE INVENTION

The present inventors extensively studied for solving the above problems of the conventional technology. As a result, they found that magnetic fine particles having a lower critical solution temperature to which at least one substance selected from biotin and avidin is immobilized does not require immobilization of an enzyme, an antibody, or the like to the polymer on the magnetic particles depending on individual intended uses and also direct binding of a nucleic acid to a protein or the like. Based on the findings, they accomplished the invention.

As is apparent from the above descriptions, an object of the invention is to provide magnetic fine particles having a lower critical solution temperature highly versatile in uses as separating agents and the like, and a method of converting a substance, a method of separating or concentrating a microorganism, a method of modifying a denatured protein, a method of detecting a nucleic acid, and a method of separating a biological substance, each using the magnetic fine particles.

The invention includes the following constitutions.

(1) Magnetic fine particles having a lower critical solution temperature, and having immobilized thereto at least one substance selected from biotin and avidin.

(2) The magnetic fine particles having a lower critical solution temperature according to the above (1), wherein said at least one substance selected from biotin and avidin is immobilized to the magnetic fine particles through a polymer having a lower critical solution temperature.

(3) Magnetic fine particles having a lower critical solution temperature, and having immobilized thereto biotin.

(4) The magnetic fine particles having a lower critical solution temperature according to the above (3), herein said biotin is immobilized to the magnetic fine particles through a polymer having a lower critical solution temperature.

(5) The magnetic fine particles having a lower critical solution temperature according to the above (3) or (4), wherein said biotin is a biotin bound to avidin (hereinafter referred to as "avidin-bound biotin").

(6) The magnetic fine particles having a lower critical solution temperature according to any one of the above (1) to (4), wherein a substance having a mutual specific action with an objective substance and having immobilized thereto avidin is bound to said biotin.

(7) The magnetic fine particles having a lower critical solution temperature according to any one of the above (1), (2), and (5), wherein a substance having a mutual specific action with an objective substance and having immobilized thereto biotin is bound to said avidin.

(8) The magnetic fine particles having a lower critical solution temperature according to the above (6) or (7), wherein said substance which has a mutual specific action with an objective substance is at least one substance selected from enzymes, proteins, nucleic acids, peptides, molecular chaperon, heat shock proteins, and antibodies.

(9) A conversion method comprising converting a substance using said magnetic fine particles having a lower critical solution temperature according to any one of the above (1) to (8).

(10) A separation or concentration method comprising separating or concentrating a microorganism using said magnetic fine particles having a lower critical solution temperature according to any one of the above (1) to (8).

(11) A modification method comprising modifying a denatured protein using said magnetic fine particles having a lower critical solution temperature according to any one of the above (1) to (8).

(12) A purification, detection or concentration method comprising purifying, detecting, or concentrating a nucleic acid using said magnetic fine particles having a lower critical solution temperature according to any one of the above (1) to (8).

(13) A detection method comprising detecting a nucleic acid by amplifying the nucleic acid obtained by the method of purifying, detecting, or concentrating the nucleic acid according to the above (12).

(14) The method of detecting a nucleic acid according to the above (13), wherein said amplification is carried out by PCR method or RT-PCR method.

(15) A separating agent containing said magnetic fine particles according to any one of the above (1) to (8).

(16) A separation method comprising separating a biological substance using said separating agent according to the above (15).

BEST MODE FOR CARRYING OUT THE INVENTION

In the present description, biotin means biotin or iminobiotin and avidin means avidin or streptoavidin.

The magnetic fine particles having an LCST (hereinafter referred to as "LCST fine particles") for use in the invention are magnetic fine particles having a nature that the magnetic fine particles dissolve in the solvent containing the magnetic fine particles when the temperature of the solvent is lower than a particular temperature and the magnetic fine particles precipitate and aggregate in the solvent when the temperature is not lower than the particular temperature. The LCST means the particular temperature. Moreover, a phenomenon that magnetic fine particles dissolve or precipitate wherein the LCST acts as a border is called an LCST characteristic.

The above-mentioned solvent is not particularly limited but specifically includes water and a liquid containing 50% by weight or more of water. Furthermore, the liquid containing 50% by weight or more of water specifically includes biological saline, a buffer solution, and the like. Moreover, the solvent may be a mixed liquid of an organic solvent such as acetone and water as far as the liquid exhibits the LCST characteristic in a polymer-containing state.

The composition or structure of the LCST magnetic fine particles for use in the invention is not particularly limited but particles wherein a polymer having an LCST is immobilized to the surface of magnetic fine particles is preferable.

Examples of the polymer having an LCST include poly-N-substituted acrylamide derivatives and their copolymers, poly-N-substituted methacrylamide derivatives and their copolymers, polyvinyl methyl ether, polypropylene oxide, polyethylene oxide, poly-N-vinylalkylamide, poly-N-isopropylacrylamide, and the like.

The magnetic fine particles to which the polymer having an LCST is immobilized are not particularly limited and the raw material may be an organic or inorganic substance as far as it exhibits magnetism at ordinary temperature. Specifically, it includes nickel oxide particles, ferrite particles, magnetite particles, cobalt iron oxide, barium ferrite, carbon steel, tungsten steel, KS steel, rare-earth cobalt magnet fine particles, hematite particles, and the like.

The particle size of the magnetic fine particles may be such a size that the magnetic fine particles are not adsorbed by a magnetic force even when the magnetic force is applied to the solvent in which the magnetic fine particles are dispersed. In the invention, the size is not particularly limited but is preferably in the range of 1 nm to 1 μm, more preferably in the range of 1 nm to 100 nm.

The process for preparing the magnetic fine particles for use in the invention is described with reference to the case of using magnetite. Magnetic magnetite fine particles having a particle size of several dozen nm can be obtained by converting magnetite into double micelles using sodium oleate and sodium dodecylbenzenesulfonate and dispersing the micelles into an aqueous solution. This process is the process described in Biocatalysis, 1991, Vol. 5, pp. 61-69.

An LCST polymer may be immobilized to the surface of magnetic fine particles by any action. That is, the action may be physical absorption or a chemical bond such as a hydrogen bond or a covalent bond. Specifically, methods for the immobilization include a method of carrying out the polymerization for obtaining an LCST polymer in the presence of magnetic fine particles, a method of bringing an LCST polymer into contact with magnetic fine particles in a solvent, a method of binding a coupling agent having a functional group such as SH group to magnetic fine particles and subjecting an LCST polymer to graft polymerization using the functional group as a starting point.

Of these, magnetic fine particles of the invention obtainable by the method of carrying out the polymerization for obtaining an LCST polymer in the presence of magnetic fine particles are preferable because the immobilized LCST polymer is hardly eliminated from the magnetic fine particles even when dissolution and precipitation/aggregation are repeatedly carried out in a liquid containing the same.

The method for immobilizing at least one substance selected from biotin and avidin to the LCST polymer immobilized to magnetic fine particles is not particularly limited and includes a method of immobilizing at least one substance selected from biotin and avidin to the LCST polymer already synthesized (hereinafter referred to as "immobilization method") and a method of introducing one of the one pair of substances by polymerizing a monomer having biotin or avidin as part of the structure and a monomer forming the LCST polymer through polymerization (hereinafter referred to as "polymerization method").

The above-mentioned immobilization method preferably uses a covalent bond, but binding utilizing an ion-complex or a charge-transfer complex, binding utilizing a biochemical affinity or the like may be used.

On the other hand, the polymerization method is preferably employed in the invention because it is relatively easy to control polymerization ratio in a polymer. The method for immobilizing biotin to the UCST polymer immobilized to magnetic fine particles is described in detail by way of illustration of the polymerization method using a monomer having biotin as part of the structure.

Examples of the monomer forming the LCST polymer through polymerization includes N-substituted acrylamide derivatives, N-substituted methacrylamide derivatives; vinyl methyl ether, propylene oxide, ethylene oxide, N-vinylalkylamide, N-isopropylacrylamide (the following general formula (1)), and the like.

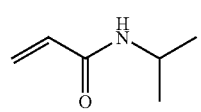

(1)

The monomer having biotin as part of the structure includes (meth)acrylamide, (meth)acrylate derivatives, and the like formed by utilizing a terminal carboxyl group of biotin, but is not limited thereto.

The monomer forming the LCST polymer to be preferably used in the polymerization method includes above-mentioned N-isopropyl acrylamide, and the monomer having biotin as part of the structure includes a polymerizable biotin derivative represented by the following general formula (2).

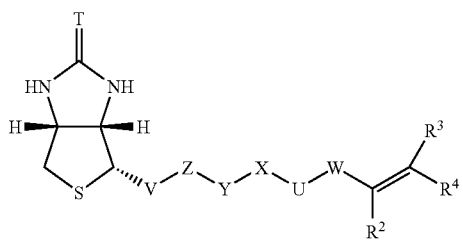

(2)

In the general formula (2), $R^2$ represents a hydrogen atom or an alkyl group. $R^3$ and $R^4$ each independently represents a hydrogen atom, an alkyl group or an aryl group. T represents an oxygen atom or =NH group. W represents a single bond or a carbonyl group, a thiocarbonyl group, or an alkylene group having 1 to 5 carbon atoms. U represents a single bond or —NH— group. X represents a single bond or a hydrocarbon group having 1 to 8 carbon atoms, an oxygen atom, or —NH— group. Y represents a single bond or a carbonyl group, a thiocarbonyl group, —NH— group, a 1,2-dioxyethylene group, or a 1,2-diaminoethylene group. Z represents a single bond or a carbonyl group, a thiocarbonyl group, an alkylene group having 1 to 5 carbon atoms, an oxygen atom, or —NH— group. V represents a single bond or an alkylene group having 1 to 5 carbon atoms.

Of the monomers represented by the following general formula (2), polymerizable biotin derivatives represented by the following general formulae (3) to (5) may be preferably used in the polymerization method.

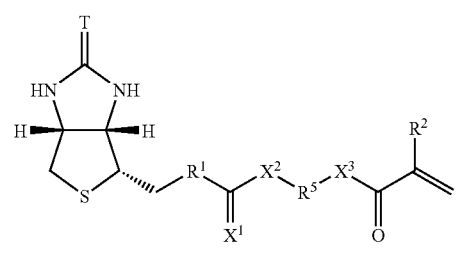

(3)

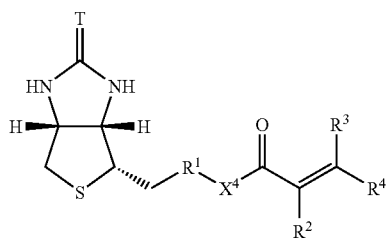

(4)

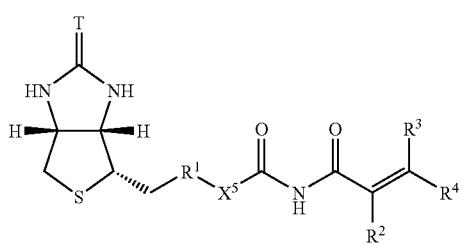

(5)

In the general formulae (3) to (5), $R^1$ represents a single bond or an alkylene group having 1 to 4 carbon atoms and $R^5$ represents an alkylene group having 2 or 3 carbon atoms. $X^1$ represents an oxygen atom or a sulfur atom, $X^2$ to $X^5$ each independently represents an oxygen atom or —NH— group. T, $R^2$, $R^3$, and $R^4$ each has the same definition as in the above general formula (2).

The polymerizable biotin derivative represented by the above general formula (3) can be generally obtained by converting the side chain carboxyl hydroxyl group of biotin or that of a biotin derivative represented by the following general formula (6) into an appropriate leaving group and then condensing the product with an acrylic derivative represented by the following general formula (7).

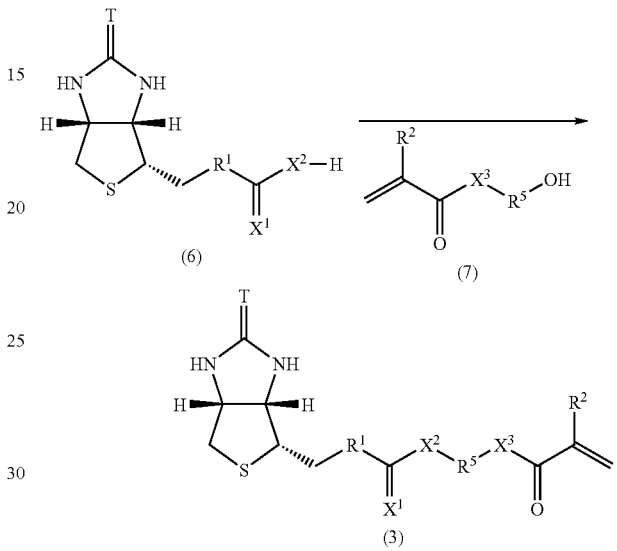

The polymerizable biotin derivative represented by the above general formula (4) can be obtained by reacting a biotin derivative represented by the above general formula (8) with an appropriate acrylating agent (including a methacrylating agent or the like; for example, an acrylating agent such as acrylic acid, acryloyl chloride, acrylic anhydride, or acryloxysuccinimide, a methacrylating agent such as methacrylic acid, methacryloyl chloride, methacrylic anhydride, or methacryloxysuccinimide, or the like).

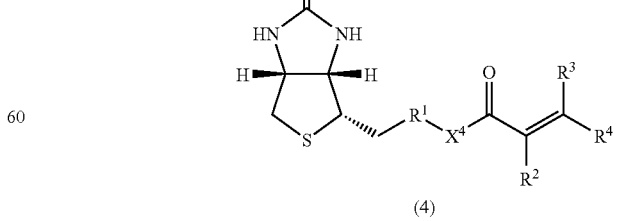

Herein, the biotin derivative represented by the above general formula (8) can be obtained by converting the hydroxyl group of an alcohol compound ($X^4$=an oxygen atom) obtainable by reducing biotin or the biotin derivative represented by the general formula (6) with an appropriate reducing agent into a functional group having a function as a leaving group and then subjecting the alcohol compound after the conversion to a substitution reaction with an amine derivative ($X^4$=—NH—).

The polymerizable biotin derivative represented by the above general formula (5) can be obtained by reacting a biotin derivative represented by the following general formula (9) with an isocyanate substance represented by the general formula (10) in an aprotic solvent such as tetrahydrofuran (THF), dimethyl sulfoxide (DMSO), ether, dimethylformamide (DMF), dichloromethane, chloroform, ethyl acetate, acetone, an aliphatic hydrocarbon, benzene, or toluene.

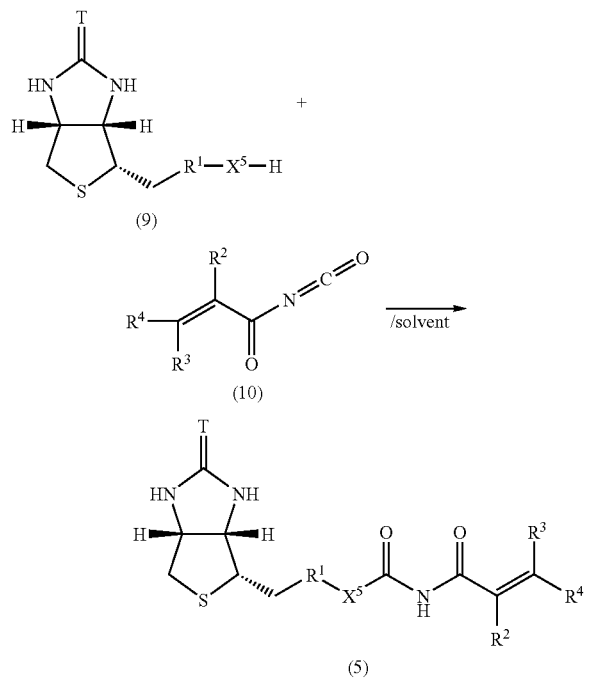

Furthermore, a polymerizable biotin derivative represented by the following general formula (11) is particularly preferably used in the polymerization method.

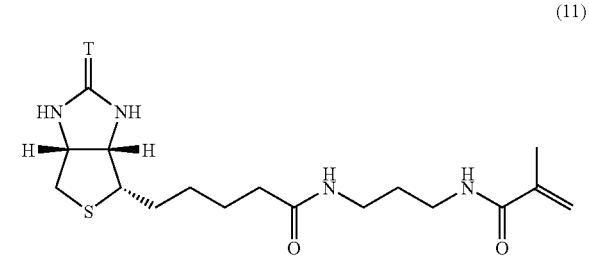

Moreover, the monomer capable of being preferably used in the polymerization method includes a biotin methacrylamide derivative represented by the general formula (12) and a biotin derivative represented by the general formula (13).

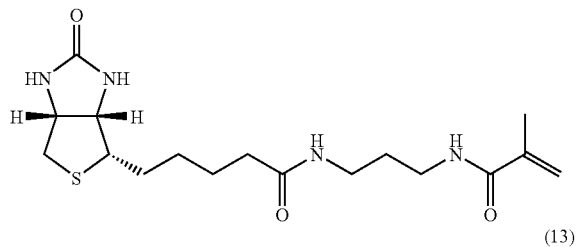

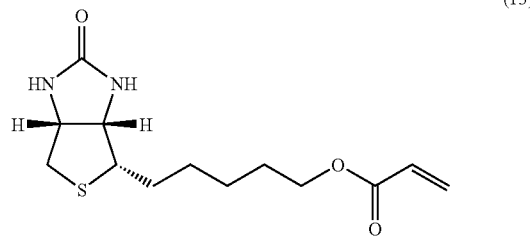

The polymerization method will be described more specifically. The above biotin monomer is added to a solution containing 0.01 to 10% by weight of a monomer forming an LCST polymer in an amount so as to be a molar ratio (a monomer forming an LCST polymer/an iminobiotin monomer) of preferably 1000/1 to 5/1, more preferably 1000/1 to 10/1, and subsequently magnetic fine particles are added thereto in an amount so as to be 0.01 to 5% by weight.

Then, polymerization is initiated by adding 0.01 to 1% by weight of a polymerization initiator (e.g., potassium persulfate) or 0.001 to 0.1% by polymerization of a polymerization accelerator (e.g., tetramethylenediamine). The polymerization may be carried out under a nitrogen atmosphere. Moreover, the solution temperature at the polymerization is not particularly limited but is preferably about 20 to 60° C. Furthermore, the molecular weight of the resulting polymer is not particularly limited but is preferably about tens of thousand to 1,000,000.

When the LCST magnetic fine particles of the invention are produced by the method of carrying out the polymerization for obtaining an LCST polymer in the presence of magnetic fine particles, contaminants such as unreacted monomers and salts coexist in the reaction solution. The contaminants may be removed by dialysis or by raising the temperature of the solution to the LCST or higher to cause aggregation, recovering aggregated matter with a magnet, and subsequently removing the resulting supernatant.

In the invention, it is sufficient to immobilize at least one substance selected from biotin and avidin, but biotin is preferable because it is difficult to immobilize avidin directly to an LCST polymer.

The method of immobilizing easily avidin to LCST magnetic fine particles is preferably a method of immobilizing biotin to an LCST polymer through biotin. That is, avidin is preferably immobilized to the LCST polymer in the form of avidin-bound biotin.

In the invention, in the case that biotin is immobilized to magnetic fine particles having an LCST, it is possible to separate and recover selectively only an objective substance to which avidin is immobilized. In the case that avidin is immobilized to magnetic fine particles having an LCST, it is possible to separate and recover selectively only an objective substance to which biotin is immobilized.

In this connection, in the case that avidin is immobilized to the LCST magnetic fine particles of the invention, a biotinylated objective substance can be separated and recovered more efficiently because it is possible to maintain the state that a maximum of three sites of four biotin-binding sites of avidin are opened.

Furthermore, conversion, separation, concentration, or recovery of a substrate is enabled in a high efficiency by magnetic fine particles obtainable by immobilizing, to the LCST magnetic fine particles of the invention to which biotin is immobilized, a substance which has a mutual specific action with an objective substance and to which avidin is immobilized, through a biotin-avidin binding, or by magnetic fine particles obtainable by immobilizing, to the LCST magnetic fine particles of the invention to which avidin is immobilized, a substance which has a mutual specific action with an objective substance and to which biotin is immobilized, through a biotin-avidin binding.

Especially, conversion, separation, concentration, or recovery of a substrate, a biotinylated objective substance, is enabled in a higher efficiency by magnetic fine particles obtainable by immobilizing, to the LCST magnetic fine particles of the invention to which avidin is immobilized, a substance which has a mutual specific action with the objective substance and to which biotin is immobilized, through a biotin-avidin binding, because it is possible to maintain the state that a maximum of three sites of four biotin-binding sites of avidin are opened.

In the invention, the substance having a mutual specific action with an objective substance is not particularly limited but specifically, it includes enzymes, proteins, nucleic acids, peptides, molecular Chaperons, heat shock proteins, antibodies, and the like.

For example, in the case that an enzyme is used as the substance having a mutual specific action with an objective substance, it is possible to convert a substrate at a faster rate as compared with the rate in an enzymatic reaction using a conventional immobilized enzyme. The enzyme to be used at that time is not particularly limited but it includes oxidoreductases, transferases, hydrolases, splitting enzymes, isomerases, enzymes for synthesis, and the like.

The substance produced by converting a substrate can be easily separated from the enzyme by raising the temperature of the solution containing the magnetic fine particles of the invention and the produced substance to precipitate only the magnetic fine particles and removing only the thus precipitated magnetic fine particles using magnetism.

In the case that an antibody is used as the substance having a mutual specific action with an objective substance, it is possible to separate or concentrate efficiently a microorganism in a solution. The antibody to be used at that time may be a monoclonal antibody or a polyclonal antibody.

The method of separating or concentrating a microorganism in a solution is not particularly limited but there may be specifically mentioned a method of adding the magnetic fine particles to a solution containing a microorganism, bringing the microorganism thoroughly into contact with the magnetic fine particles, then raising the temperature of the solution to precipitate only the magnetic fine particles which have adsorbed the microorganism, and removing only the thus precipitated magnetic fine particles using magnetic force. By this method, it is possible to separate or concentrate a microorganism in a solution easily.

For example, when the antibody to be used is a salmonella antibody, since only salmonella in a food suspension can be easily separate or concentrate, it is possible to prepare a microorganism-assaying kit or diagnostic agent exhibiting a high sensitivity by combining the magnetic fine particles of the invention to which any antibody is immobilized and an appropriate detecting reagent.

In the case of the LCST magnetic fine particles of the invention wherein a molecular chaperon or heat shock protein is used as the substance having a mutual specific action with an objective substance, since stability of an enzyme or antibody in absolution is enhanced, repeated separation thereof becomes possible, and hence production of proteins or substances at an industrial level can be assisted. Generally, since a protein such as a molecular chaperon is expensive, it is difficult to use it at an industrial level.

There may be mentioned a method of adding the magnetic fine particles of the invention, in which a nucleic acid is used as the substance having a mutual specific action with an objective substance, to a solution containing a nucleic acid, bringing the magnetic fine particles thoroughly into contact with the nucleic acid, then raising the temperature of the solution to precipitate only the magnetic fine particles which have adsorbed the nucleic acid, and removing only the thus precipitated magnetic fine particles using magnetism. By this method, it is possible to separate or concentrate a nucleic acid in a solution easily. By this method, it is possible to separate or concentrate a nucleic acid in a solution easily. Moreover, the method of separating or concentrating a nucleic acid is applicable to purification, concentration, detection, or the like of a specific gene.

Moreover, purification, detection, or concentration of any nucleic acid can be easily carried out by effecting thoroughly hybridization in a mixed solution containing two or more kinds of nucleic acids and the magnetic fine particles, then raising the temperature of the mixed solution to aggregate and recover the particles together with the nucleic acids, and again lowering the temperature.

For example, target DNA or mRNA can be concentrated or purified by using a biotinylated DNA having a sequence complementary to the target DNA or biotinylated polythymine. A nucleic acid can be detected in a good sensitivity by amplifying the resulting nucleic acid according to any of various gene-amplifying methods. The method of amplifying the nucleic acid is not particularly limited but PCR method or RT-PCR method may be preferably used in the invention.

The separating agent of the invention is not particularly limited as far as it contains the LCST magnetic fine particles of the invention, but the content of the magnetic fine particles in the separating agent is preferably in the range of 1 to 100% by weight, particularly preferably in the range of 2 to 30% by weight.

The other components include ferrite particles, magnetite particles, hematite particles, and the like.

The use of the separating agent of the invention enables a facile separation of a microorganism, a nucleic acid, a protein, an antigen, an endocrine-disrupting chemical or the like.

EXAMPLES

The present invention will be illustrated in greater detail with reference to the following Examples, but the invention should not be construed as being limited thereto.

Example 1

Preparation of Magnetic Fine Particles

Magnetic fine particles are prepared according to the following method.

In a 1 L flask, 83.4 g of ferrous sulfate (heptahydrate) and 10.4 g of sodium nitrite were thoroughly mixed with 500 ml of distilled water, followed by 20 minutes of stirring at 40° C. Thereafter, 125 ml of concentrated ammonia was added thereto and insoluble matter was collected and washed twice with distilled water to obtain magnetite. The resulting magnetite was added to 500 ml of distilled water in a 1 L flask and the temperature of the solution was raised to 80° C. Then, 7.5 g of sodium oleate was added thereto, followed by 20 minutes of stirring at the same temperature. Thereafter, pH of the solution was adjusted to 5.5 and the resulting insoluble matter was collected by filtration and washed twice with distilled water to obtain magnetite having an oleic acid layer. The magnetite was again added into a 1 L flask, 500 ml of distilled water was added, and the temperature of the solution was raised to 70° C. Then, 7.5 g of sodium dodecylbenzenesulfonate was added thereto and the whole was stirred overnight to obtain magnetic fine particles.

Example 2

Preparation of LCST Magnetic Fine Particles

Using the above magnetic fine particles, LCST magnetic fine particles were prepared according to the following method.

Into a 300 ml flask were added 4 ml of the magnetic fine particles prepared in Example 1, 0.488 g of N-isopropylacrylamide, 12.7 mg of N-biotinyl-N'-methacryloyltrimethyleneamide, and 94 ml of distilled water, followed by thorough stirring at room temperature. Thereto was added 0.1 g of potassium persulfate, followed by 6 hours of stirring at room temperature. The resulting solution was dialyzed for one day and night to obtain a solution of LCST magnetic fine particles to which biotin was immobilized.

The lower critical solution temperature (LCST) of the resulting solution was measured to be 31° C. The LCST hardly changed in a physiological saline and in 100 mM phosphate buffer (pH 7.0). In this connection, the LCST was measured using transmittance of visible light.

Example 3

Separation of Avidin From Aqueous Solution

In a test tube, 50 μl of the solution of LCST magnetic fine particles obtained in Example 2, 50 μl of 1.0% avidin solution, 100 μl of 1.0 M sodium phosphate buffer (pH 7.0), and 800 μl of distilled water were thoroughly mixed and then the temperature of the solution was raised to 31° C. or higher. The aggregate was recovered with neodi-magnet (4300 G), and 100 μl of the supernatant was taken out and subjected to denaturation treatment with sodium dodecyl sulfate (SDS). Then, disappearance of the band corresponding to avidin in the supernatant was confirmed by SDS-polyacrylamide gel electrophoresis (SDS-PAGE).

Example 4

Specific Separation of Avidin From Albumen

In a test tube, 50 μl of the solution of LCST magnetic fine particles obtained in Example 2, 50 μl of 1.0% avidin solution, 100 μl of 1.0 M sodium phosphate buffer (pH 7.0), 450 μl of distilled water, and 400 μl of 2.5% albumen solution were thoroughly mixed and then the temperature of the solution was raised to 31° C. or higher. The aggregate was recovered with neodi-magnet (4300 G), and 100 μl of the supernatant was taken out and subjected to denaturation treatment with SDS. Then, disappearance of only the band corresponding to avidin in the supernatant was confirmed by SDS-PAGE.

Example 5

Immobilization of Avidin-Immobilized Enzyme to LCST Magnetic Fine Particles

One hundred μl of the solution of LCST magnetic fine particles obtained in Example 2, 1000 μl of a commercially available avidin-immobilized peroxidase solution (1 mg/ml), 100 μl of 1.0 M sodium phosphate buffer (pH 7.0), and 700 μl of distilled water were added and thoroughly mixed. The resulting solution was heated and the aggregate was recovered with a magnet. After 1900 μl of the supernatant was removed, 1900 μl of 0.1 M phosphate buffer (pH 7.0) was newly added to prepare a solution of the LCST magnetic fine particles to which avidin-immobilized peroxidase was immobilized. The solution dissolved at the LCST or lower and aggregated at the LCST or higher. The temperature of the solution was changed by means of a constant temperature bath, and operations of dissolution, aggregation, and recovery with a magnet were carried out. The activity of the peroxidase in each supernatant was measured according to the method of measuring the activity of peroxidase shown in the following. In this connection, after the recovery of the magnetic fine particles with a magnet, 1900 μl of the supernatant was removed and 1900 l of 0.1 M phosphate buffer (pH 7.0) was newly added each time.

(Method of Measuring Peroxidase Activity)

In a cell of an absorptiometer, 100 μl of 100 mM hydrogen peroxide, 100 μl of 50 mM phenol, 100 μl of 50 mM 4-aminoantipyrine, 100 μl of 1.0 M sodium phosphate buffer (pH 7.0), and 580 μl of distilled water were mixed beforehand, and 20 μl of a sample was added thereto. After the mixture was again thoroughly mixed, the product was measured by an increase of the absorption at 500 nm. In this connection, the above operations were carried out at 30° C.

The following Table-1 shows the results of measuring enzymatic activity of the supernatant in the case that aggregation and dissolution were repeatedly carried out according to the above method. The enzymatic activity was represented by specific activity wherein the activity at the first dissolution was regarded as 100.

TABLE 1

| Number of repetition (time) | Peroxidase activity at dissolution of magnetic fine particles (%) | Peroxidase activity of supernatant after aggregation and recovery of magnetic fine particles (%) |
|---|---|---|
| 1 | 100 | 10 |
| 2 | 99 | 5 |
| 3 | 103 | 3 |
| 5 | 106 | 3 |
| 10 | 102 | 2 |
| 20 | 101 | 0 |

From these results, it was revealed that the activity of the avidin-immobilized peroxidase immobilized to the magnetic fine particles was hardly decreased even when the peroxidase was subjected to repeated dissolution and aggregation together with the magnetic fine particles and repetition of the operations.

Example 6

Immobilization of Biotin-Immobilized Enzyme to Avidin-Immobilized LCST Magnetic Fine Particles In order to obtain avidin-immobilized LCST magnetic fine particles wherein three sites of biotin-binding sites of avidin were free, 50 µl of the solution of LCST magnetic fine particles obtained in Example 2 was thoroughly mixed with 500 µl of 1.0% avidin solution, 100 µl of 1.0 M sodium phosphate buffer (pH 7.0), and 350 µl of distilled water in a test tube and then the temperature of the solution was raised to 31° C. or higher by placing the test tube in a constant temperature bath at 40° C. The aggregate was recovered with neodi-magnet (4300 G) to obtain avidin-immobilized LCST magnetic fine particles wherein the biotin-binding sites other than the binding site to the polymer were free.

One hundred µl of the solution of the avidin-immobilized magnetic fine particles, 1000 µl of a commercially available avidin-immobilized peroxidase solution (1 mg/ml), 100 µl of 1.0 M sodium phosphate buffer (pH 7.0), and 700 µl of distilled water were added and thoroughly mixed. The resulting solution was heated and the aggregate was recovered with a magnet. After 1900 µl of the supernatant was removed, 1900 µl of 0.1 M phosphate buffer (pH 7.0) was newly added to prepare avidin-immobilized LCST magnetic fine particles to which biotin-immobilized peroxidase was immobilized.

The following Table-2 shows the results of measuring enzymatic activity of the supernatant in the case that dissolution, aggregation, and recovery were repeatedly carried out in a similar manner to Example 5 using the LCST magnetic fine particles. The enzymatic activity was also represented by specific activity wherein the activity at the first dissolution was regarded as 100.

TABLE 2

| Number of repetition (time) | Peroxidase activity at dissolution of magnetic fine particles (%) | Peroxidase activity of supernatant after aggregation and recovery of magnetic fine particles (%) |
| --- | --- | --- |
| 1 | 100 | 1 |
| 2 | 101 | 1 |
| 3 | 99 | 1 |
| 5 | 96 | 0 |
| 10 | 97 | 0 |
| 20 | 91 | 0 |

From these results, it was revealed that the activity of the biotin-immobilized peroxidase bound to the LCST magnetic fine particles to which avidin was immobilized was hardly decreased even when the peroxidase was subjected to repeated dissolution and aggregation together with the magnetic fine particles and repetition of the operations.

Example 7

Immobilization of Molecular Chaperon to LCST Magnetic Fine Particles

A commercially available heat shock protein HSP70 to which biotin was immobilized was thoroughly mixed with 100 mM sodium phosphate buffer (pH 7.0) and the 5 µl of the mixture was taken out. After denaturation treatment, the band of HSP70 was confirmed by SDS-PAGE. Subsequently, 50 µl of the avidin-immobilized LCST magnetic fine particles wherein the biotin-binding sites other than the binding site to the polymer were free prepared in Example 6 was added thereto and the whole was thoroughly mixed. Thereafter, as in Example 3, the solution was heated to aggregate the magnetic fine particles, which was recovered with a magnet. HSP70 in the supernatant was similarly investigated by SDS-PAGE to confirm that HSP70 was absent in the supernatant and was bound to avidin immobilized to the magnetic fine particles.

Example 8

Method of Separating and Concentrating Microorganism

A commercially available biotin-immobilized salmonella antibody was immobilized to LCST magnetic fine particles as in Example 6. The immobilization was confirmed using SDS-PAGE. Subsequently, 1 ml of the solution of the magnetic fine particles was added to 20 ml of a bacteria suspension which was adjusted so as to contain the salmonella in a rate of one bacteria/ml and the whole was thoroughly mixed. Thereafter, as in Example 3, the solution was heated to aggregate the magnetic fine particles, which was recovered with a magnet. The supernatant was removed to make a 1 ml solution. The solution was sterilized beforehand and added to 20 ml of a brain-heart infusion agar medium and the whole was rapidly mixed. Then, the mixture was spread in a petri dish and allowed to stand to cool until the agar became hard, followed by 48 hours of incubation at 37° C. The following Table-3 shows the results of measuring the number of colonies after 48 hours. These all the operations were carried out in a clean workstation. Additionally, the number of bacteria in 1 ml of the bacteria suspension originally prepared was similarly measured as a control without adding the magnetic fine particles.

TABLE 3

|  | Control | Use of LCST magnetic fine particles of the invention |
| --- | --- | --- |
| Number of colonies | 1 | 21 |

From the results, it was apparent that salmonella was concentrated by the magnetic fine particles

Example 9

Immobilization of Nucleic Acid to Magnetic Fine Particles Exhibiting LCST

To 500 µl of a commercially available biotinylated labeled DNA fragment (50 to 1000 bp) were added 450 µl of distilled water and 50 µl of avidin-immobilized LCST magnetic fine particles prepared in Example 6 wherein the biotin-binding sites other than the binding site to the polymer were free, and the whole was thoroughly mixed. Thereafter, as in Example 3, the solution was heated to aggregate the magnetic fine particles, which was recovered with a magnet. The confirmation of the DNA fragment in the supernatant by agarose gel electrophoresis suggested that all the DNA fragments were bound to the magnetic fine particles.

Through a similar experiment on RNA, the binding to the magnetic fine particles was confirmed.

While the invention has been described in detail and with reference to specific embodiments thereof, it will be apparent to one skilled in the art that various changes and modifications can be made therein without departing from the spirit and scope thereof.

This application is based on Japanese Patent Application No. 2000-249774 filed on Aug. 21, 2000 and the entire content thereof is incorporated herein by reference.

INDUSTRIAL APPLICABILITY

The magnetic fine particles of the invention having a lower critical solution temperature to which at least one substance selected from biotin and avidin is immobilized does not require immobilization of an enzyme, an antibody, or the like to the polymer on the magnetic particles depending on individual intended uses and also does not require direct binding of a nucleic acid to a protein or the like. Therefore, the magnetic fine particles are highly versatile in the uses as separating agents or the like.

In addition, a method of converting a substance, a method of separating or concentrating a microorganism, a method of modifying a denatured protein, a method of detecting a nucleic acid, and a method of separating a biological substance using the magnetic fine particles of the invention having a lower critical solution temperature enable an efficient achievement of individual purposes.

The invention claimed is:

1. A method for converting an objective substance into a converted material and recovering the converted material, comprising providing magnetic fine particles having immobilized thereto a copolymer that has a lower critical solution temperature, wherein the copolymer comprises a unit derived from a comonomer containing biotin as a constituent, immobilizing a substance having a mutual specific action with an objective substance to the magnetic fine particles to which biotin is bound, mixing the resulting magnetic fine particles and the objective substance to create a solution, in which the substance and the objective substance react, precipitating the magnetic fine particles by raising the temperature of the solution to a temperature not lower than the lower critical solution temperature of the magnetic fine particles, and recovering the converted material, wherein the biotin-containing comonomer is a biotin methacrylamide derivative represented by formula (12):

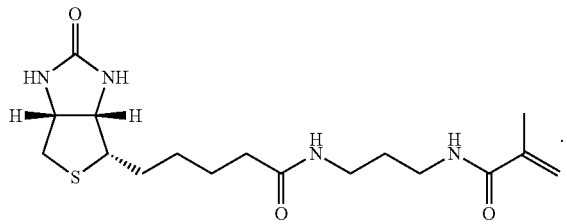

(12)

2. The method according to claim 1, wherein the biotin is biotin bound to avidin.

3. The method according to claim 1, wherein the substance having a mutual specific action with an objective substance has avidin immobilized thereto, and is bound to the biotin.

4. The method according to claim 1, wherein the substance having a mutual specific action with an objective substance is at least one substance selected from the group consisting of enzymes, proteins, nucleic acids, peptides, molecular chaperon, heat shock proteins, and antibodies.

5. The method according to claim 2, wherein the substance having a mutual specific action with an objective substance has biotin immobilized thereto, and is bound to said avidin.

6. The method according to claim 3, wherein the substance which has a mutual specific action with an objective substance is at least one substance selected from the group consisting of enzymes, proteins, nucleic acids, peptides, molecular chaperon, heat shock proteins, and antibodies.

7. The method according to claim 5, wherein the substance which has a mutual specific action with an objective substance is at least one substance selected from the group consisting of enzymes, proteins, nucleic acids, peptides, molecular chaperon, heat shock proteins, and antibodies.

* * * * *